United States Patent [19]
Preiss et al.

[11] Patent Number: 6,020,381
[45] Date of Patent: Feb. 1, 2000

[54] USE OF 2-METHYLAMINO-2-PHENYLCYCLOHEXANONE FOR THE TREATMENT OF PROTOZOAN INFECTIONS

[75] Inventors: Detlef Preiss; Akos Tatar, both of Berlin, Germany

[73] Assignee: Detleg Preiss, Germany

[21] Appl. No.: 08/729,962

[22] Filed: Oct. 15, 1996

Related U.S. Application Data

[62] Division of application No. 08/404,171, Mar. 2, 1995.

[30] Foreign Application Priority Data

Mar. 15, 1994 [DE] Germany ............... 44 09 671

[51] Int. Cl.$^7$ .................................................. A61K 31/135
[52] U.S. Cl. ............................................... 514/647
[58] Field of Search ............................... 514/647

[56] References Cited

U.S. PATENT DOCUMENTS 3,254,124  5/1966  Stevens ................................. 260/570.5

OTHER PUBLICATIONS

Pauli et al., "A case for the inclusion of a protozoan test in aquatic toxicity assessment using Tetrahymena," The Science of the Total Environment, pp. 779–786 (1993).
Pauli etal 120 CA 156043y 1994.

*Primary Examiner*—Russell Travers
*Attorney, Agent, or Firm*—Webb Ziesenheim Bruening Logsdon Orkin & Hanson, P.C.

[57] ABSTRACT

This invention relates to the use of 2-methylamino-2-phenylcyclohexanone and of pharmaceuticals which contain this active agent in combination with physiologically acceptable solid or liquid supporting materials or diluents for treating bacterial, fungal, virus or protozoan infections as well as for immunomodulation.

2 Claims, 3 Drawing Sheets

USE OF 2-METHYLAMINO-2-PHENYLCYCLOHEXANONE FOR THE TREATMENT OF PROTOZOAN INFECTIONS

This application is a division of Ser. No. 08/404,171, filed Mar. 2, 1995.

FIELD OF INVENTION

This invention relates to the use of 2-methylamino-2-phenylcyclohexanone for treating bacterial, fungal, virus or protozoan infections, as well as for immunomodulation.

BACKGROUND OF INVENTION

A great number of pharmaceutic agents is used in today's medical practice to treat infections. These infections quite frequently impair the immunological system while a weakened immunological system, on the other hand, attracts infections.

A whole lot of so-called wide-spectrum therapeutic agents that act against a great number of different strains of bacteria and fungus cultures is available to treat bacterial and fungal infections.

Only few agents, however, are known in the field of virus infections, these agents being effective only specifically, i.e. against specific viruses.

Infections caused by protozoa provide a similar picture. Only specifically active therapeutic agents are available that address a specific strain of pathogens only.

As infections are frequently characterized by an accelerated progress of the disease because pathogens multiply exponentially, it is desirable to have therapeutic agents on hand that are suited for initial medication due to their wide activity spectrum.

This requirement is currently met to a satisfactory extent with regard to bacterial and fungal infections only. But there have been no such wide-spectrum agents available as yet for the field of virus and protozoan infections.

SUMMARY OF INVENTION

It is therefore a problem to be solved by this invention to provide an agent that is suited for treating a great number of infections caused by various bacteria, fungi, viruses or protozoa, as well as for immunomodulation. This agent should be characterized by low toxicity, good tolerability, and a wide therapeutic spectrum.

The present invention solves this problem by using 2-methylamino-2-phenylcyclohexanone or its physiologically tolerable salts for the treatment of bacterial, fungal, virus and protozoan infections, and for immunomodulation.

DETAILED DESCRIPTION OF INVENTION

Figure 1A:
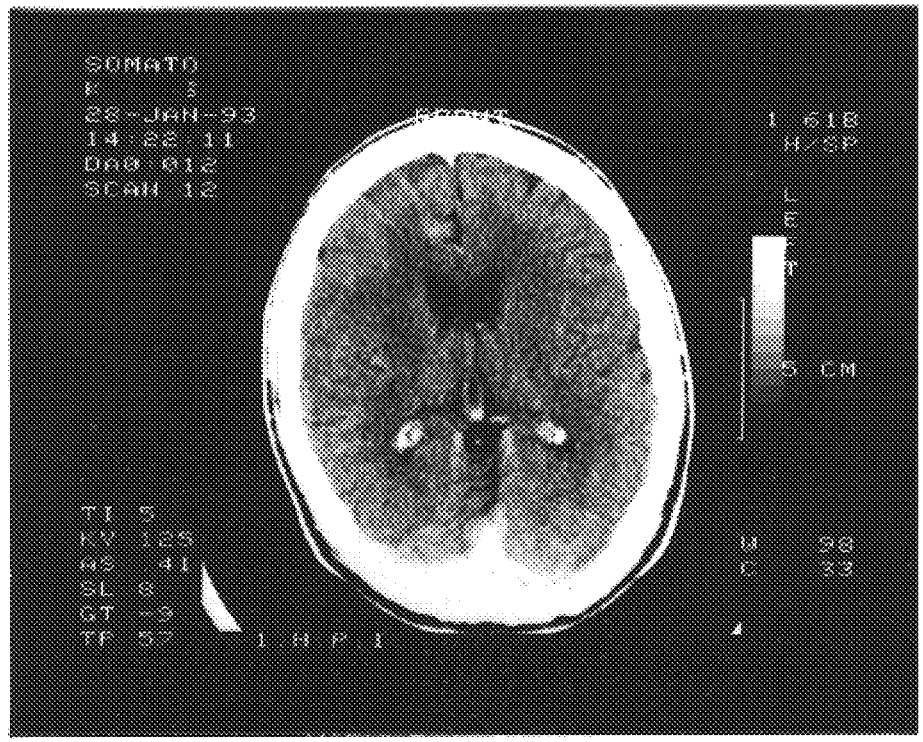
FIGS. 1a and 2a are computer tomograms of various planes of the patient's head before MPCH treatment.

It was found, surprisingly, that 2-methylamino-2-phenylcyclohexanone is effective in a great number of bacterial, fungal, virus and protozoan diseases, and in immunomodulation.

2-methylamino-2-phenyl-cyclohexanone (MPCH) has been known from U.S. Pat. spec. No. 3,254,124. It describes MPCH as a compound showing cataleptic activity. MPCH has not been used as a pharmaceutical up to now.

Surprisingly, it was found that MPCH is effective against a number of various herpes viruses. It could be shown that MPCH is effective against herpes labialis, herpes genitalis, herpes zoster, and herpes simplex. Furthermore, activity against cytomegalic viruses (CMV) and HIV viruses could be proved.

With HIV infections, in particular, it was surprisingly found that associated opportunist infections are restrained to a great extent as well. It is known that HIV-infected people frequently suffer from Plaut's angina, candidiasis, cytomegalic disease, pneumocystia, and herpetic infections.

These associated infections were also restrained using MPCH, which dramatically improved the condition of HIV-infected patients.

Another object of the present invention is the use of 2-methylamino-2-phenylcyclohexanone or its physiologically tolerable salts for the production of pharmaceuticals. For this purpose, 2-methylamino-2-phenylcyclohexanone is optionally converted into an acid addition salt, preferably into a salt of a physiologically tolerable acid.

Common physiologically tolerable inorganic and organic acids include: hydrochloric acid, hydrobromic acid, phosphoric acid, sulfuric acid, oxalic acid, maleic acid, fumaric acid, lactic acid, tartaric acid, malic acid, citric acid, salicylic acid, adipic acid, and benzoic acid. Other usable acids are described, for example, in Fortschritte der Arzneimittelforschung, vol. 10, pages 224–225, Birkhäuser Verlag Based and Stuttgart, 1966, and in Journal of Pharmaceutical Sciences, vol. 66, pages 1–5 (1977).

The acid addition salts are obtained, as a rule, in a generally known way by mixing the free base or its solutions with the respective acid or its solutions in an organic solvent, for example, a lower alcohol such as methanol, ethanol, n-propanol or isopropanol, or a lower ketone such as acetone, methylethyl ketone, or methyl isobutyl ketone, or an ether such as diethyl ether, tetrahydrofuran, or dioxane. Mixtures of the above solvents can be used to improve crystallization. In addition, physiologically tolerable aqueous solutions of acid addition salts of MPCH can be produced in an aqueous acid solution.

The acid addition salts of MPCH can be converted into the free base in a generally known way, e.g. using alkalies or ion exchangers. Other salts can be gained from the free base by reacting it with inorganic or organic acids, especially such acids that are suitable for forming therapeutically applicable salts. These and other salts of the new compound as, for example, its picrate, can also be used for cleaning the free base. For this, the free base is converted into a salt, said salt is separated, and the base released again from that salt.

Another object of the present invention are pharmaceuticals for oral, rectal, subcutaneous, intravenous or intramuscular administration which contain MPCH or its acid addition salt as active substance along with the common supporting materials and diluents.

The pharmaceuticals of the invention are produced in a known way using the usual solid or liquid supporting materials or diluents and the common adjuvants used in pharmaceutical engineering, and at an appropriate dosage depending on the intended form of administration. Preferred formulations are those forms suitable for oral administration, for example, tablets, film tablets, dragées, capsules, pills, powder, solutions, suspensions, or repository forms.

Consideration may also be given to parenteral formulations such as injection solutions. Suppositories represent another form of application.

Tablets may be obtained, for example, by intermixing the active substance with known adjuvants, for example, inert diluents such as dextrose, sugar, sorbitol, mannitol, polyvinylpyrrolidone, disintegrating agents which swell rapidly on contact with body fluids and thereby quickly disintegrate the tablets and disperse the medicament such as maize starch or alginic acid, binders such as starch or gelatin, lubricants such as magnesium stearate or talcum and/or materials by which to produce a time release effect, such as carboxyl polymethylene, carboxymethyl cellulose, cellulose acetate phthalate or polyvinyl acetate. Tablets may consist of several layers. A multitude of appropriate formulations can be found in the formulary known to all pharmaceutical chemists: Remington's Pharmaceutical Sciences, 15th Edition (1975), Mack Publishing Company, Easton, Pa. 18042.

Dragees may be produced accordingly by coating cores manufactured in analogy to tablet manufacture using agents generally applied to dragee coating, for example, polyvinylpyrrolidone or shellac, Arabic gum, talcum, titanium dioxide, or sugar. The coating of the dragée may also consist of several layers in which the adjuvants mentioned in the paragraph on tablets can be used.

Solutions or suspensions containing the active agent of the invention may additionally contain flavor-enhancing substances such as saccharin, cyclamate or sugar, or aromatic substances such as vanillin or orange extract. They may also contain suspension-supporting adjuvants such as sodium carboxymethyl cellulose, or preservatives such as p-hydroxybenzoates. Capsules containing active agents may be produced, for example, by mixing the active agent with an inert substrate such as lactose or sorbitol, and encapsulating such mixture in gelatin capsules.

Appropriate suppositories may be made by mixing the active substance with the suitable substrates, such as neutral fats or polyethylene glycol and their derivatives.

The invention is illustrated by the following examples:

EXAMPLE 1

Preppreparation of 2-methylamino-2-phenyl-cyclohexanone-hydrochloride

Step 1

14 g (196 mmol) of bromine were added by dropping, and under stirring, to 14 g (80 mmol) of cyclopentyl ketone dissolved in 200 ml of anhydrous ether. The resulting solution was refluxed for 30 minutes. The solvent was removed under reduced pressure, the remaining yellow oil dissolved in 20 ml of petroleum ether, and crystallized out.

Yield 14 g (69% of theor. q'ty) 1-benzoyl-1-bromocyclopentane Melting point: 28–30° C.

Step 2

12 g (47 mmol) of 1-benzoyl-1-bromocyclopentane were mixed with 30 ml of liquid methyl amine at −20° C. The reaction mixture was allowed to warm up to room temperature within one hour. After adding 50 ml of ether, the salt that has formed was filtered off by suction, the solvent was removed under reduced pressure, and the remaining crystals were dried.

Yield 2.95 g (31% of theor. q'ty) of 1-hydroxy-cyclopentyl phenyl-ketone-N-methylimine Melting point: 72–74° C.

Step 3

2.95 g (14.5 mmol) of 1-hydroxy-cyclopentyl-phenyl-ketone N-methylimine were dissolved in 30 ml of decaline and refluxed for 2 hours. After cooling, the reaction mixture was mixed with HCl gas saturated 2-propanol in slight molar excess. The products were filtered off by suction and recrystallized from 2-propanol/ester.

Yield 3.3 g of the title compound, MPCH Melting point: 255–257° C.

EXAMPLE 2

Treatment of toxoplasmosis

A patient in a bad state of health suffering from multifocal cerebral toxoplasmosis which was established using computer tomography was treated with MPCH as follows: 2 mg of MPCH twice a week for eight weeks, followed by no medication for 4 weeks, and 2 mg of MPCH twice a week for two weeks.

Figure 1B:
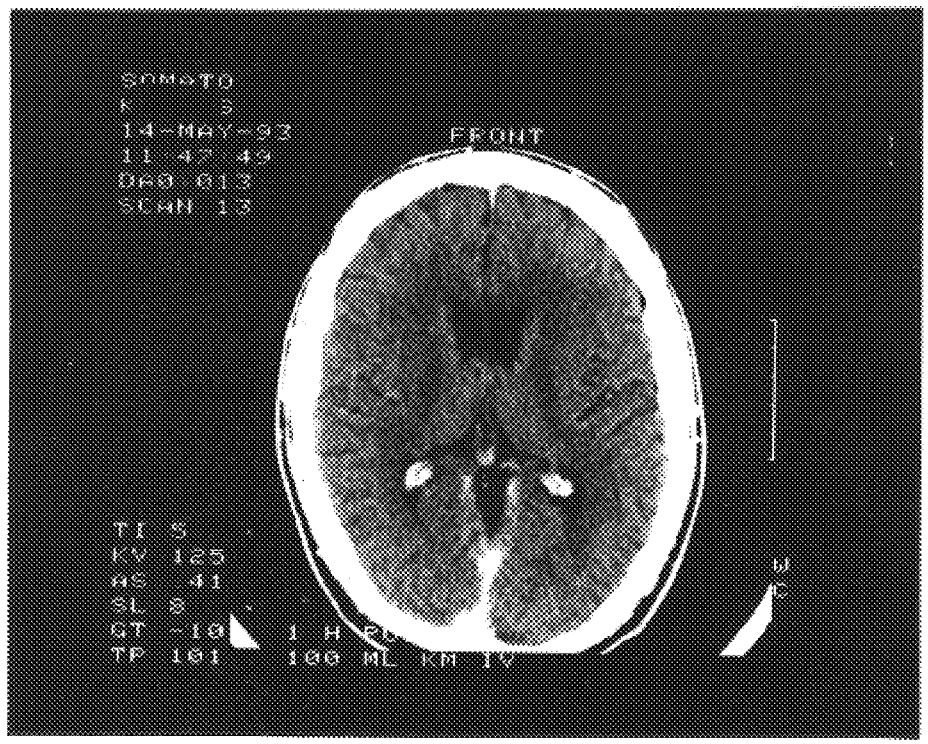
FIGS. 1b and 2b are computer tomograms of these areas after MPCH treatment.
Figure 2A:
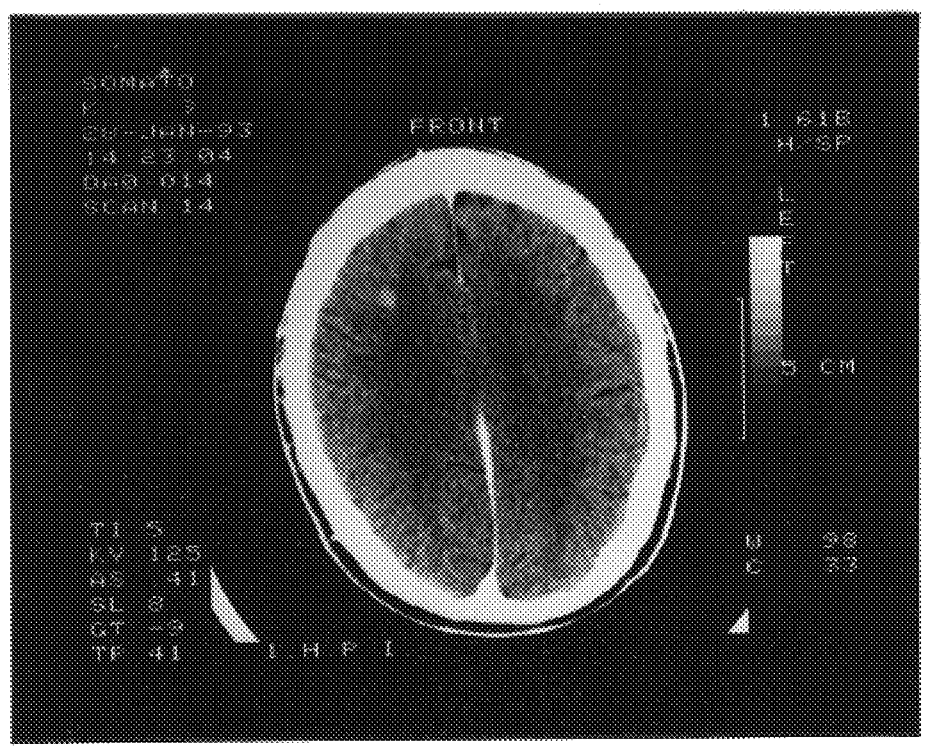
Figure 2B:
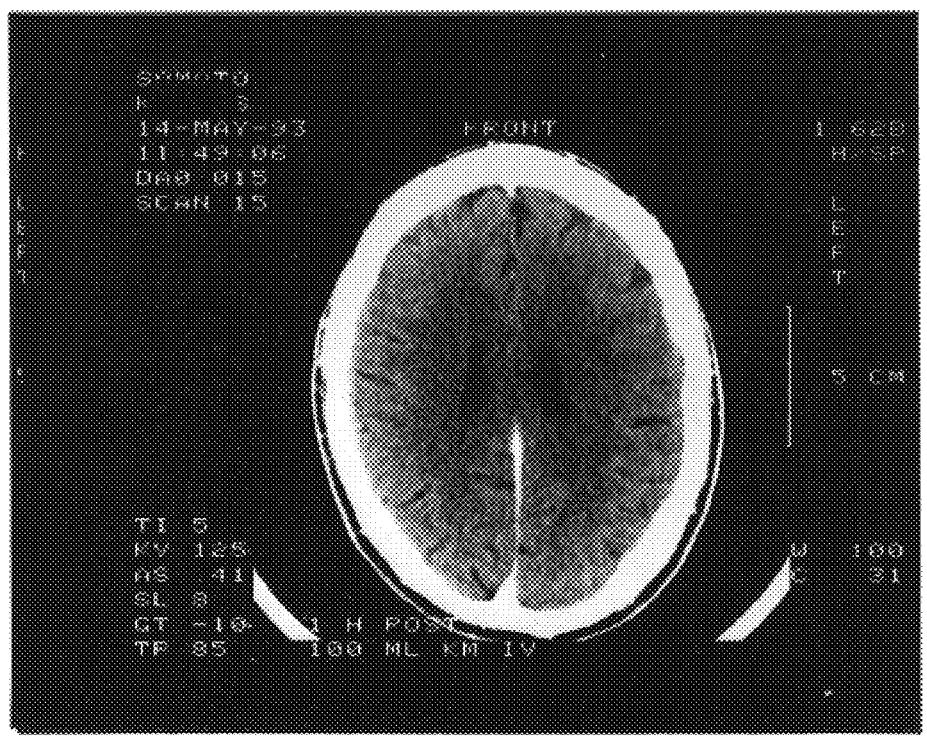

The patient's general condition improved noticeably within one month. FIGS. 1a, 1b and 2a, 2b are supervisory computer tomograms of said patient's cerebrum which show that the foci of toxoplasmosis were reduced significantly after treatment with MPCH. FIGS. 1a and 2a are computer tomograms of various planes of the patient's head before MPCH treatment. Foci of toxoplasmosis can be spotted in FIGS. 1a and 2a in the frontal third of the left half of the brain. FIGS. 1b and 2b are computer tomograms of these areas after MPCH treatment. They show a clear or even complete regression of said foci of toxoplasmosis.

EXAMPLE 3

Treatment of cytomegalovirus diseases (CMV)

A febrile patient in a generally bad state of health showing a generalized swelling of a lymph node as well as a CMV-related conjunctivitis (serum test) was treated on the first, third, fourth and fifth day with 2 mg of MPCH respectively. The patient was free from fever on the third day, the swellings of the lymph nodes were gone on the fourth day, and conjunctivitis had vanished on the sixth day when the patient was in a good state of health again.

EXAMPLE 4

Treatment of herpetic infections

Figure 3:
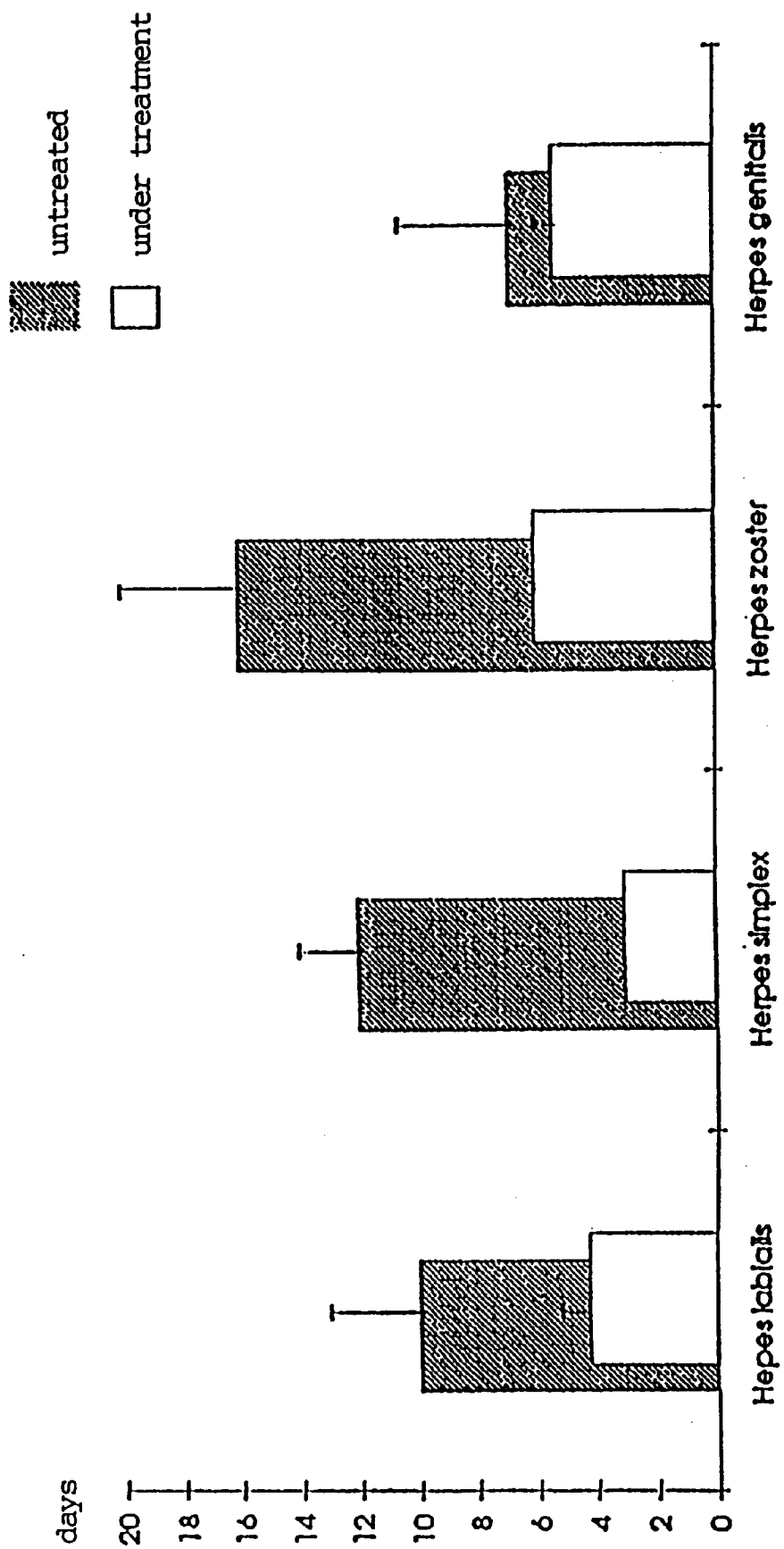
FIG. 3 illustrates, in bar chart form, statistical data demonstrating the efficacy of the compositions and methods of the invention.
Figure 1A:
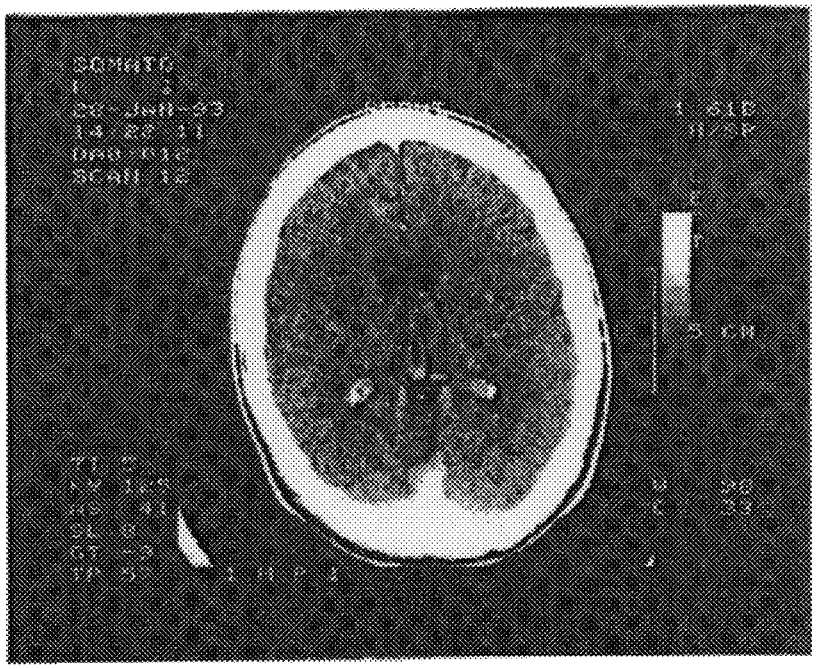
Figure 1B:
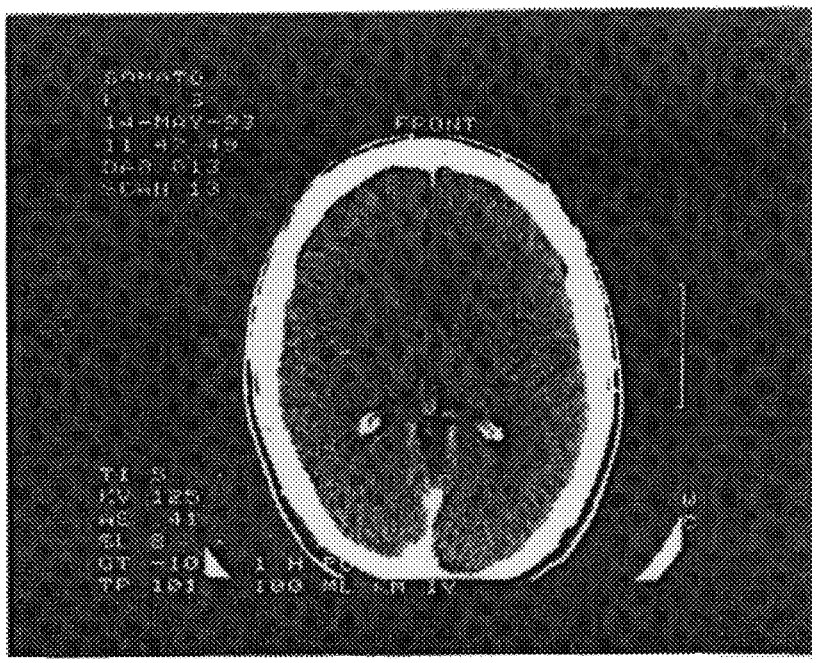
Figure 2A:
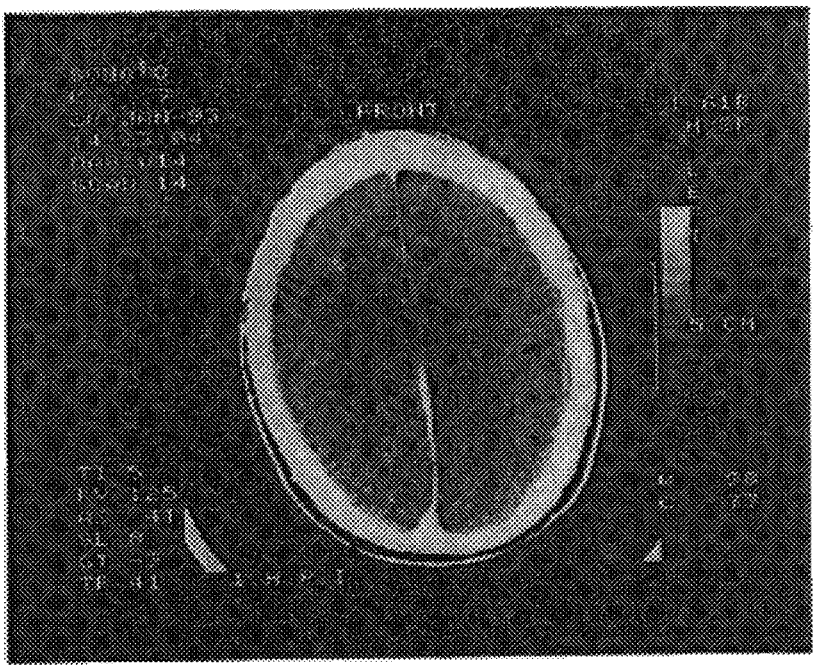
Figure 2B:
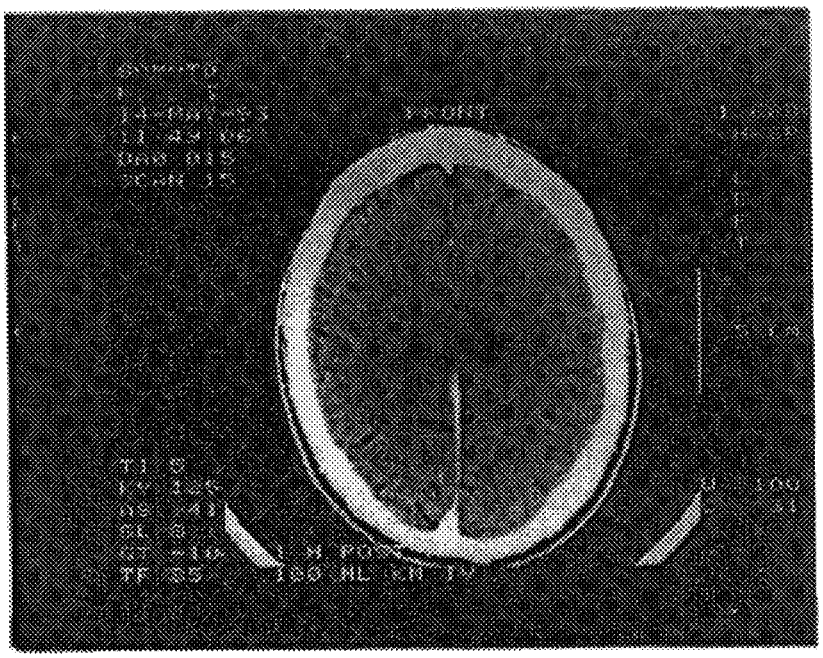

Various groups of patients suffering from lip herpes, genital herpes, herpes zoster and herpes simplex were treated by administering MPCH. The dose was 2 mg of MPCH per day for about 4–5 days. At the end of the therapy, the diseases cured more speedily to a statistically significant extent (cf. FIG. 3).

EXAMPLE 5

Treatment of HIV diseases

A patient in a bad state of health who had been HIV infected for more than 10 years and was suffering from an unspecified mycoplasmal infection and perimyocarditis as well as neuropathies was administered 2 mg of MPCH twice a week for six weeks. His general condition improved significantly; the patient gained weight and had no other infections.

A repeated attack of infections occurred after nine months and included Plaut's angina, candidiasis, cytomegalic disease, and lip herpes. The patient was again treated twice a week, each time by administering 2 mg of MPCH. He recovered completely from all infections within the time of the therapy.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A method of treating a patient having a protozoan infection, comprising:

administering to the patient a pharmacologically effective dosage of unsubstituted 2-methylamino-2-phenyl-cyclohexanone (MPCH) or its physiologically tolerable salts.

2. A method of treating a patient as set forth in claim 1, wherein the infection is toxoplasmosis.

* * * * *

UNITED STATES PATENT AND TRADEMARK OFFICE
CERTIFICATE OF CORRECTION

PATENT NO.    : 6,020,381
DATED         : February 1, 2000
INVENTOR(S)   : Preiss et al.

It is certified that error appears in the above-identified patent and that said Letters Patent is hereby corrected as shown below:

Title page,
The title page should be deleted to appear as per attached title page.

Drawings,
Drawing Sheets 1-3 should be deleted to appear as per attached Drawing Sheets 1-3.

Please delete columns 1-6 and substitute columns 1-4 as per attached.

Signed and Sealed this

Seventeenth Day of December, 2002

JAMES E. ROGAN
*Director of the United States Patent and Trademark Office*

United States Patent [19]

Preiss et al.

[11] Patent Number: 6,020,381
[45] Date of Patent: Feb. 1, 2000

[54] USE OF 2-METHYLAMINO-2-PHENYLCYCLOHEXANONE FOR THE TREATMENT OF PROTOZOAN INFECTIONS

[75] Inventors: Detlef Preiss; Akos Tatar, both of Berlin, Germany

[73] Assignee: Detleg Preiss, Germany

[21] Appl. No.: 08/729,962

[22] Filed: Oct. 15, 1996

Related U.S. Application Data

[62] Division of application No. 08/404,171, Mar. 2, 1995.

[30] Foreign Application Priority Data

Mar. 15, 1994 [DE] Germany .............. 44 09 671

[51] Int. Cl.$^7$ ........................................ A61K 31/135
[52] U.S. Cl. ........................................ 514/647
[58] Field of Search ........................................ 514/647

[56] References Cited

U.S. PATENT DOCUMENTS 3,254,124  5/1966  Stevens ........................ 260/570.5

OTHER PUBLICATIONS

Pauli et al., "A case for the inclusion of a protozoan test in aquatic toxicity assessment using Tetrahymena," The Science of the Total Environment, pp. 779–786 (1993).
Pauli etal 120 CA 156043y 1994.

*Primary Examiner*—Russell Travers
*Attorney, Agent, or Firm*—Webb Ziesenheim Bruening Logsdon Orkin & Hanson, P.C.

[57] ABSTRACT

This invention relates to the use of 2-methylamino-2-phenylcyclohexanone (MPCH) and of pharmaceuticals which contain this active agent in combination with physiologically acceptable solid or liquid supporting materials or diluents for treating protozoan infections.

2 Claims, 3 Drawing Sheets

USE OF 2-METHYLAMINO-2-PHENYLCYCLOHEXANONE FOR THE TREATMENT OF PROTOZOAN INFECTIONS

This application is a division of Ser. No. 08/404,171, filed Mar. 2, 1995.

FIELD OF INVENTION

This invention relates to the use of 2-methylamino-2-phenylcyclohexanone for treating protozoan infections.

BACKGROUND OF INVENTION

A great number of pharmaceutic agents is used in today's medical practice to treat infections. These infections quite frequently impair the immunological system while a weakened immunological system, on the other hand, attracts infections.

Few agents are known that act against infections caused by protozoa, and there is only a very limited number of agents available for therapy that in many cases address a specific strain of pathogens only.

Plasmodium, for example, which causes different forms of malaria, is up to now mostly treated with chinoline derivatives. Every year millions of people die of malaria. In toxoplasmosis, another protozoic infection, mostly sulfonamides are used for therapy.

As infections are frequently characterized by an accelerated progress of the disease because pathogens multiply exponentially, it is desirable to have therapeutic agents on hand that are suited for initial medication due to their wide activity spectrum.

This requirement is currently met to a satifactory extent with regard to bacterial and fungal infections only. But there have been no such wide-spectrum agents available as yet for the field of protozoan infections.

SUMMARY OF INVENTION

It is therefore a problem to be solved by this invention to provide an agent that is suited for treating a great number of infections caused by various protozoa. This agent should be characterized by low toxicity, good tolerability, and a wide therapeutic spectrum.

The present invention solves this problem by using 2-methylamino-2-phenylcyclohexanone or its physiologically tolerable salts for the treatment of protozoan infections.

BRIEF DESCRIPTION OF DRAWINGS

FIGS. 1a and 2a are computer tomograms of various planes of the patient's head before MPCH treatment;

FIGS. 1b and 2b are computer tomograms of these areas after MPCH treatment;

DETAILED DESCRIPTION OF INVENTION

It was found, surprisingly, that 2-methylamino-2-phenylcyclohexanone is effective in a number of protozoan diseases.

2-methylamino-2-phenylcyclohexanone (MPCH) has been known from U.S. Pat. No. 3,254,124. It describes MPCH as a compound showing cataleptic activity. MPCH has not been used as a pharmaceutical up to now.

One object of the present invention is the use of 2-methylamino-2-phenylcyclohexanone or its physiologically tolerable salts for the production of pharmaceuticals. For this purpose, 2-methylamino-2-phenylcyclohexanone is optionally converted into an acid addition salt, preferably into a salt of a physiologically tolerable acid.

Common physiologically tolerable inorganic and organic acids include: hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid. Other useable acids are described, for example, in Fortschritte der Arzneimittelforschung, vol. 10, pp 224–225, Birkhäuser Verlag Basel and Stuttgart, (1966), and in Journal of Pharmaceutical Sciences, vol. 66, pages 1–5 (1977).

The acid addition salts are obtained, as a rule, in a generally known way by mixing the free base or its solutions with the respective acid or its solutions in an organic solvent, for example, a lower alcohol such as methanol, ethanol, n-propanol or isopropanol, or a lower ketone, such as acetone, methylethyl ketone or methyl isobutyl ketone, or an ether such as diethyl ether, tetrahydrofuran, or dioxane. Mixtures of the above solvents can be used to improve crystallization. In addition, physiologically tolerable aqueous solutions of acid addition salts of MPCH can be produced in an aqueous acid solution.

The acid addition salts of MPCH can be converted into the free base in a generally known way, e.g. using alkalies or ion exchangers. Other salts can be gained from the free base by reacting it with inorganic or organic acids, especially such acids that are suitable for forming therapeutically applicable salts. These and other salts of the new compund as, for example, its picrate, can also be used for cleaning the free base. For this, the free base is converted into a salt, said salt is separated, and the base released again from the salt.

Another object of the present invention are pharmaceuticals for oral, rectal, subcutaneous, intravenous or intramuscular administration which contain MPCH or its acid addition salt as active substance along with the common supporting materials and diluents.

The pharmaceuticals of the invention are produced in a known way using the usual solid or liquid supporting materials or diluents and the common adjuvants used in pharmaceutical engineering, and at an appropriate dosage depending on the intended form of administration. Preferred formulations are those forms suitable for oral administration, for example, tablets, film tablets, dragees, capsules, pills, powder, solutions, suspensions, or repository forms.

Consideration may also be given to parenteral formulations such as injection solutions. Suppositories represent another form of application.

Tablets may be obtained, for example, by intermixing the active substance with known adjuvants, for example, inert diluents such as dextrose, sugar, sorbitol, mannitol, polyvinylpyrrolidone, disintegrating agents which swell rapidly on contact with body fluids and thereby quickly disintegrate the tablets and disperse the medicament such as maize starch or alginic acid, binders such as starch or gelatin, lubricants such as magnesium stearate or talcum and/or materials by which to produce a time release effect, such as carboxyl polymethylene, carboxymethyl cellulose, cellulose acetate phthalate or polyvinyl acetate. Tablets may consist of several layers. A multitude of appropriate formulations can be found in the formulary known to all pharmaceutical chemists: Remington's Pharmaceutical Sciences, 15th Edition (1975), Mack Publishing Company, Easton, Pa. 18042.

Dragées may be produced accordingly by coating cores manufactured in analogy to tablet manufacture using agents generally applied to dragée coating, for example, polyvinylpyrrolidone or shellac, Arabic gum, talcum, titanium dioxide, or sugar. The coating of the dragée may also consist of several layers in which the adjuvants mentioned in the paragraph on tablets can be used.

Solutions or suspensions containing the active agent of the invention may additionally contain flavour-enhancing substances such as saccharin, cyclamate or sugar, or aromatic substances such as vanillin or orange extract. They may also contain suspension-supporting adjuvants such as sodium carboxymethyl cellulose, or preservatives such as p-hydroxybenzoates. Capsules containing active agents may be produced, for example, by mixing the active agent with an inert substrate such as lactose or sorbitol, and encapsulating such mixture in gelatin capsules.

Appropriate suppositories may be made by mixing the active substance with the suitable substrates, such as neutral fats or polyethylene glycol and their derivatives.

The invention is illustrated by the following examples:

EXAMPLE 1

Preparation of 2-methylamino-2-phenylcyclohexanone-hydrochloride

Step 1

14 g (196 mmol) of bromine were added by dropping, and under stirring, to 14 g (80 mmol) of cyclopentyl ketone dissolved in 200 ml of anhydrous ether. The resulting solution was refluxed for 30 minutes. The solvent was removed under reduced pressure, the remaining yellow oil dissolved in 20 ml of petroleum ether, and crystallized out.

Yield 14 g (69% of theor. q'ty) 1-benzoyl-bromocyclopentane

Melting point: 28–30° C.

Step 2

12 g (47 mmol) of 1-benzoyl-bromocyclopentane were mixed with 30 ml of liquid methyl amine at −20° C. The reaction mixture was allowed to warm up to room temperature within one hour. After adding 50 ml of ether, the salt that has formed was filtered off by suction, the solvent was removed under reduced pressure, and the remaining crystals were dried.

Yield 2.95 g (31% of theor. q'ty) of 1-hydroxy-cyclopentylphenyl-ketone-N-methylimine Melting point: 72–74° C.

Step 3

2.95 g (14.5 mmol) of 1-hydroxy-cyclopentylphenyl-ketone-N-methylimine were dissolved in 30 ml of decaline and refluxed for 2 hours. After cooling, the reaction mixture was mixed with HCl gas saturated 2-propanol in slight molar excess. The products were filtered off by suction and recrystallized from 2-propanol/ester.

Yield 3.3 g of the title compound, MPCH

Melting point: 255–257° C.

EXAMPLE 2

Treatment of Toxoplasmosis

A patient in a bad state of health suffering from multifocal cerebral toxoplasmosis which was established using computer tomography was treated with MPCH as follows: 2 mg of MPCH twice a week for eight weeks, followed by no medication for 4 weeks, and 2 mg of MPCH twice a week for two weeks.

The patient's general condition improved noticeably within one month. FIGS. 1a, 1b and 2a, 2b are supervisory computer tomograms of said patient's cerebrum which show that the foci of toxoplasmosis were reduced significantly after treatment with MPCH. FIGS. 1a and 2a are computer tomograms of various planes of the patient's head before MPCH treatment. Foci of toxoplasmosis can be spotted in FIGS. 1a and 2a in the frontal third of the left half of the brain. FIGS. 1b and 2b are the computer tomograms of these areas after MPCH treatment. They show a clear or even complete regression of said foci of toxoplasmosis.

While the invention has been described in connection with specific embodiments thereof, it will be understood that it is capable of further modification, and this application is intended to cover any variations, uses, or adaptations of the invention following, in general, the principles of the invention and including such departures from the disclosure as come within known or customary practice in the art to which the invention pertains and as may be applied to the essential features hereinbefore set forth, and as fall within the scope of the invention and the limits of the appended claims.

What is claimed is:

1. A method of treating a patient having a protozoan infection, comprising:

administering to the patient a pharmacologically effective dosage of unsubstituted 2-methylamino-2-phenylcyclohexanone (MPCH) or its physiologically tolerable salts.

2. A method of treating a patient as set forth in claim 1, wherein the infection is toxoplasmosis.

* * * * *